United States Patent
Uppal et al.

(10) Patent No.: US 10,335,444 B2
(45) Date of Patent: Jul. 2, 2019

(54) METHOD FOR EXTRACTING HIGH CONTENT OF CHLOROGENIC ACIDS FROM GREEN COFFEE BEANS

(71) Applicant: Pawan Kumar Goel, Panchkula-(Haryana) (IN)

(72) Inventors: Dalip Uppal, Haryana (IN); Ashok Sharma, Haryana (IN); Kiran Tewari, Haryana (IN)

(73) Assignee: Pawan Kumar Goel, Panchkula (IN)

( * ) Notice: Subject to any disclaimer, the term of this patent is extended or adjusted under 35 U.S.C. 154(b) by 340 days.

(21) Appl. No.: 15/100,055

(22) PCT Filed: Jun. 10, 2015

(86) PCT No.: PCT/IN2015/000236
§ 371 (c)(1),
(2) Date: May 27, 2016

(87) PCT Pub. No.: WO2015/189857
PCT Pub. Date: Dec. 17, 2015

(65) Prior Publication Data
US 2017/0007658 A1   Jan. 12, 2017

(30) Foreign Application Priority Data

Jun. 13, 2014 (IN) .......................... 1614/DEL/2014

(51) Int. Cl.
*A61K 36/74* (2006.01)
*A23F 5/02* (2006.01)
*A23L 33/105* (2016.01)

(52) U.S. Cl.
CPC ............... *A61K 36/74* (2013.01); *A23F 5/02* (2013.01); *A23L 33/105* (2016.08); *A23V 2002/00* (2013.01); *A61K 2236/00* (2013.01); *A61K 2236/15* (2013.01); *A61K 2236/33* (2013.01)

(58) Field of Classification Search
None
See application file for complete search history.

(56) References Cited

U.S. PATENT DOCUMENTS

| | | | |
|---|---|---|---|
| 4,409,253 A | 10/1983 | Morrison, Jr. et al. | |
| 2005/0147728 A1* | 7/2005 | Shioya | A23L 2/02 426/590 |
| 2011/0097429 A1 | 4/2011 | Segond et al. | |
| 2012/0189750 A1 | 7/2012 | Chien et al. | |
| 2017/0327776 A1* | 11/2017 | Chien | A23C 9/1307 |

FOREIGN PATENT DOCUMENTS

| | | | |
|---|---|---|---|
| EP | 2 725 007 A1 | | 4/2014 |
| FR | 2734479 | * | 11/1996 |
| JP | 2005 263632 | * | 9/2005 |
| WO | 01/66106 A1 | | 9/2001 |
| WO | 02/085397 A1 | | 10/2002 |
| WO | 2006/108578 A1 | | 10/2006 |

OTHER PUBLICATIONS

Dibert K. et al. Solvent Extraction of Oil and Chlorogenic Acid from Green Coffee, Part 1 J of Food Engineering vol. 10: pp. 1-11, 1989. (Year: 1989).*
Dibert K. et al. Solvent Extraction of Oil and Chlorogenic Acid from Green Coffee, Part 2. J of Food Engineering 10(3)199-214, 1989. (Year: 1989).*
Moreira I. et al. Solvent Effects on Extraction of Chlorogenic Acids, Caffeine and Trigonelline from Coffea arabica. Quimica Nova 37 (1)39-43, 2014. (Year: 2014).*
Ky, C. et al. Comparison of Five Purification Methods for Chlorogenic Acids in Green Coffee Beans. J Agricultural Food Chemistry 45:786-790, 1997. (Year: 1997).*
Rubach M. et al. Activity Guided Fractionation to Characterize a Coffee Beverage . . . J Agricultural Food Chem 58(7)4153-4161, 2010. (Year: 2010).*
Ramalakshmi K. et al. Antioxidant Potential of Low Grade Coffee Beans. Food Research Int 41(1)96-103, 2008. (Year: 2008).*
Kamal Ibtisam., "Optimization of Instant Controlled Pressure Drop Dic-Assisted-Solvent Extraction of Total Phenols of Green Coffee Beans.", Journal of Food Studies, vol. 2, No. 1, (20130000 ) p. 42-61, URL:http://www.macrothink.org/journal/index.php/jfs/article/download/2013/3379, (Sep. 14, 2015), XP055242667 [X] 1-3. entire document [Y] 1, 4-9 DOI: http://dx.doi.org/10.5296/jfs.v2i1.2013.
Extended European Search Report dated Jan. 22, 2018 for Application No. EP 15 80 6081.

* cited by examiner

*Primary Examiner* — Ralph J Gitomer
(74) *Attorney, Agent, or Firm* — Ladas & Parry LLP

(57) ABSTRACT

An extract from green coffee beans is disclosed which contains polyphenols and bioactive compounds e.g. Chlorogenic acids in a significantly higher concentration (70-80%) than in extracts of prior art methods (40-50%). The extract has greater ability to quench oxidative stress and destroy free radicals and offers health benefits due to its anti-obesity, anti-diabetic, antihypertensive, anti-tumor and anti-acid properties. The higher concentration of bioactive compounds has been achieved by use of polar solvents having polarity less than that of alcohols used for extraction. The use of such solvents of lower polarity such as n-Butyl alcohol, ethyl acetate or acetone results in extraction of enriched Chlorogenic acid fractions into the extract, leaving polar impurities behind in aqueous medium. The extract obtained has significantly higher content of polyphenols and chlorogenic acids ranging from 70-80% and a distinctive HPLC profile.

5 Claims, 7 Drawing Sheets

CHEMICAL RESOURCES

Sample Information

| | |
|---|---|
| Acquired by | : Admin |
| Sample Name | : Green Coffee Bean Extract |
| Sample ID | : Upgraded Sample (70.0%) |
| Tray# | : 1 |
| Vail# | : 3 |
| Injection Volume | : 10 ul |
| Data Filename | : COFEX-04.lcd |
| Method Filename | : chlorogenic acid.lcm |
| Batch Filename | : COFEX.lcb |
| Report Filename | : GENERAL FORMAT.lcr |
| Date Acquired | : 6/5/2015 1:50:10 PM |
| Date Processed | : 6/8/2015 12:51:52 PM |

Fig. 2

Detector A CH1 330nm

PeakTable

| Peak # | Name | Ret. Time | Area | Area % |
|---|---|---|---|---|
| 1 | | 5.146 | 389777 | 4.017 |
| 2 | 5-CQA | 7.467 | 4485965 | 46.227 |
| 3 | | 7.960 | 989792 | 10.200 |
| 4 | | 12.079 | 1079017 | 11.119 |
| 5 | | 18.968 | 787532 | 8.115 |
| 6 | | 20.035 | 648590 | 6.684 |
| 7 | | 21.713 | 1088994 | 11.222 |
| 8 | | 23.635 | 115862 | 1.194 |
| 9 | | 24.947 | 26788 | 0.276 |
| 10 | | 25.417 | 91876 | 0.947 |
| Total | | | 9704193 | 100.000 |

Fig. 2 (continued)

CHEMICAL RESOURCES

Sample Information

| | |
|---|---|
| Acquired by | : Admin |
| Sample Name | : Green Coffee Bean Extract |
| Sample ID | : Routine Sample (45.0%) |
| Tray# | : 1 |
| Vail# | : 2 |
| Injection Volume | : 10 ul. |
| Data Filename | : COFEX-02.lcd |
| Method Filename | : chlorogenic acid.lcm |
| Batch Filename | : COFEX.lcb |
| Report Filename | : GENERAL FORMAT.lcr |
| Date Acquired | : 6/5/2015 12:28:40 PM |
| Date Processed | : 6/9/2015 12:33:06 PM |

Fig. 3

Detector A CH1 330nm

| Peak # | Name | Ret Time | Area | Area % |
|---|---|---|---|---|
| 1 | | 5.123 | 1058626 | 16.489 |
| 2 | | 6.438 | 174374 | 2.716 |
| 3 | | 6.749 | 55754 | 0.868 |
| 4 | | 7.086 | 78723 | 1.226 |
| 5 | 5-CQA | 7.454 | 1615522 | 25.163 |
| 6 | | 7.926 | 1689934 | 26.322 |
| 7 | | 12.046 | 903883 | 14.079 |
| 8 | | 18.979 | 290690 | 4.528 |
| 9 | | 20.054 | 146882 | 2.288 |
| 10 | | 21.717 | 341255 | 5.315 |
| 11 | | 23.605 | 39536 | 0.616 |
| 12 | | 24.927 | 9658 | 0.150 |
| 13 | | 25.409 | 15299 | 0.238 |
| Total | | | 6420135 | 100.000 |

PeakTable

Fig. 3 (continued)

METHOD FOR EXTRACTING HIGH CONTENT OF CHLOROGENIC ACIDS FROM GREEN COFFEE BEANS

CROSS-REFERENCE TO RELATED APPLICATION

This U.S. application claims priority under 35 U.S.C. 371 to, and is a U.S. National Phase application of, the International Patent Application No. PCT/IN2015/000236, filed 10 Jun. 2015, which claims priority from Indian Patent Application No. 1614/DEL/2014 dated 13 Jun. 2014, the disclosures of which are incorporated in their entirety by reference herein.

FIELD OF INVENTION

The present invention relates to the field of phyto-chemistry (plant chemistry). More specifically, it relates to a natural product extract having beneficial health effects i.e. green coffee bean extract and method thereof. The extract has significantly higher content of the bioactive compounds i.e. Chlorogenic acids, than disclosed in any of the commercially available extracts, till date and is applicable for ingredients of food and drink, medicines, cosmetics, or the like. The invention also discloses its production method, using green coffee beans as the source, though method is equally applicable to any natural source rich in Chlorogenic acids, including roasted coffee beans.

BACKGROUND OF THE INVENTION

Coffee has traditionally been consumed primarily for its taste and aroma and the stimulating effect of caffeine. The two main commercially cultivated species are *Coffea canephora* (predominantly a form known as '*robusta*') and *Coffea arabica*.

Coffee and its Health Benefits

It is known that coffee is a complex mixture of many hundreds of compounds several of which are phenolic compounds, which, in combination, form a unique and pleasing aroma and taste desired by many consumers (WO 2006108578 A1). Furthermore, coffee is consumed not only for its desirable flavor but often for other reasons, such as to increase short-term mental alertness.

The positive health impact of coffee has been studied over many decades and, for a long time it has been known that certain of these coffee compounds are capable of providing benefits to the consumer, especially greater mental alertness through the ingestion of caffeine. However, it is less well known to consumers that certain coffee compounds are excellent anti-oxidants and that, weight for weight, coffee can potentially provide significantly more antioxidants to the consumer than, for example, a well-known source of anti-oxidants such as green tea.

Potential health benefits of coffee bean derived phyto-chemicals include prevention of several chronic and degenerative diseases, such as cancer, cardiovascular disorders, diabetes and Parkinson's disease and also management of obesity. Whatever the extracting agent, the beans may be extracted more than once to enhance the process and obtain greater yields of phenolic compounds.

Not only are green coffee beans a source of beneficial phenolic compounds, but unit weight per unit weight, green coffee beans produce more beneficial phenolic compounds, and in a more beneficial constituency than that obtained in the form of extracts from green tea.

Phenolic compounds are a large and diverse group of molecules, which includes many different families of aromatic secondary metabolites in plants. Phenolic compounds derived from green coffee beans, are known to be antioxidants and anti-tumor agents. The phenolic acids viz. chlorogenic acid, caffeic acid, para-coumaric acid and eugenol have been shown to exert cancer preventive activities in animal models.

Despite the presence of phenolic compounds in coffee beans, and their known beneficial properties, phenolic compounds are conventionally obtained as extracts from green tea. This appears to be because coffee bean roasting processes reduce phenolic content in coffee beans between 40% and 80%, and no one has heretofore considered obtaining phenolic compounds from green coffee beans. Analysis by the present inventors indicate that green coffee beans which initially contain 4% phenolic acids contain respectively, 2% phenolic acids when light roasted, 1% when medium roasted, and less than 0.5% when dark roasted. This clearly represents a significant loss of beneficial compounds through the roasting process.

Hence, it is of immense benefit to mankind to provide a new and therapeutic preparation in form of green coffee bean extract of present invention which has powerful anti-oxidant, anti-tumor and anti-obesity properties owing to significantly higher content (70-80%) of the bioactive compounds responsible for the therapeutic benefits viz. Chlorogenic acids. It will likewise be of benefit to provide such improved preparations and/or new and more prolific methods for obtaining or producing such preparations on a commercial level, including that from other sources rich in Chlorogenic acids, including roasted coffee beans.

Chlorogenic Acid Content in Coffee Beans

US 2002/0160067 A1 discloses that the total chlorogenic acid (different types of Chlorogenic acids are present in extracts and their combined concentration is referred to as total Chlorogenic content) content of green arabica beans is typically 6.9% and in *robusta* variety it is typically 10%. A number of different chlorogenic acids are present—5-caffeoylquinic acid is present in the largest amount. Dicaffeoyl and feruloyl quinnic acids are also present together with the 3 and 4-isomers of monocaffeoylquinic acid. Green coffee beans typically contain 1.3% diterpenes in arabica and 0.2% diterpenes in green robusta. The diterpenes are cafestol and kahweol. Various sterols and tocopherols are also present in the lipid part of green beans. Alkanoylated 5-hydroxytryptamines (the Japanese compound) in the wax on the outer surface of the green beans are present at 500-1000 mg/kg (or 0.5-1%). Trigonelline is present at 1.1% is arabica and 0.65% in robusta. Trigonelline is transformed somewhat into nicotinic acid. Apart from chlorogenic acids, the main acids present in significant quantities are quinic, malic, citric, lactic, pyruvic, succinic and glycolic.

Importance of Chlorogenic Acids in Coffee

Chlorogenic acid is the main phenolic acid in coffee and a very important anti-oxidant. Chlorogenic acids in coffee are mainly mono- and di-esters of quinic acid and phenolic groups (e.g. caffeic, ferulic, coumaric, methoxycinnamic) attached to different positions. They have important health benefits, as below:

i. Anti-Oxidant activity—Chlorogenic acids have been shown to have antioxidant activity in vitro (e.g. radical scavenging, LDL oxidation resistance, DNA damage protection)

ii. Anti-mutagenic effect—Significant anti-mutagenic effect of such acids has been shown in vivo on large intestine, liver and tongue in rats and hamsters.

iii. Anti-acid: Chlorogenic acids are also able to reduce systemic acid secretion in the stomach protecting the gastric mucosa against irritations possibly responsible for heartburn.

iv. Anti-Obesity: Scientific studies have shown that chlorogenic acid enriched instant coffee appears to have a significant effect on the absorption and utilization of glucose from the diet. This effect, if the coffee is used for an extended time, may result in reduced body mass and body fat when compared with the use of normal instant coffee. (*J Int Med Res.* 2007 November-December; 35 (6): 900-8). Various studies have suggested that chlorogenic acid slows absorption of fat from food intake and also activates metabolism of extra fat. A study on the anti-obesity effects of green coffee bean extract rich in chlorogenic acid was published in January 2012 in the Diabetes, Metabolic Syndrome and Obesity journal. The researchers followed a group of 16 adults who supplemented their diet with a special green coffee bean extract of chlorogenic acids at different dosages (either 700 or 1050 milligrams per day) for 12 weeks. All 16 adults were considered overweight, as demonstrated by a BMI of greater than 25 (a normal BMI is between 18.5 and 25). The subjects lost an average of almost 18 pounds—this was 10% of their overall body weight and 4.4% of their overall body fat.

v. Anti-hypertensive: Reduces high blood pressure and helps maintain blood pressure in normal range. (Zhao, Y.; Wang, J.; Ballevre, O.; Luo, H.; Zhang, W. (2011). "Antihypertensive effects and mechanisms of chlorogenic acids." Hypertens Res. 35 (4): 370-4. doi: 10.1038/hr.2011.195. PMID 22072103).

vi. Anti-diabetic: Help maintain blood glucose levels in the normal range. Chlorogenic acid has specifically been shown to inhibit an enzyme, glucose-6-phosphatase, that promotes the formation of glucose (sugar) in the liver. Hence, chlorogenic acid in coffee may be responsible, at least in part, for the reduced risk of glycemic disorders, like diabetes, with long-term coffee consumption.

From the health and nutritional perspective, it is desirable that consumers should be able to benefit from the positive health aspects of coffee identified above and so it would be highly advantageous to maximize the amount of chlorogenic acids available in coffee products. In this context, the present invention has achieved a remarkable technical advantage of significantly improving the Chlorogenic acid content of green coffee bean extracts to 70-80% compared to only 20-50% present in existing extracts.

The method by elaborating and disclosing the specific mechanism by which such an increase has been made possible, has enhanced the applicability of the same in improving the Chlorogenic acid content of extracts from other sources.

US 2002/0160067 A1 discloses that chlorogenic acid is suspected to be beneficial in preventing cardiovascular disease, has chemopreventative effect on rat stomach cancer and inhibits methylazoxymethanol-induced large intestinal tumors in hamsters. In vivo assays show that one third of chlorogenic acid and almost all caffeic acid is absorbed in the small intestine of humans. This implies that part of the chlorogenic acid from foods will enter into the blood circulation, but most will reach the colon. Caffeic acid seems to be more bioavailable. (Olthof et al J Nutr 2001 January; 131 (1): 66-71). Coffee contains phenolic acids which are mainly esters of quinic acid with different amount of caffeyl groups attached to its different positions. Chlorogenic acid, which is the main phenolic acid in coffee, is able to protect the gastric mucosa against irritations, and, therefore, improves the digestibility of foods, beverages and medicaments. The improved digestibility is expressed through a much reduced systemic acid secretion (such as causes heartburn, etc.) which has been found to be directly dependent on an increased level of chlorogenic acid content in roasted coffee.

Loss of chlorogenic acids during coffee processing: Conventional coffee process methods, where all of the beans that contribute to an end product are roasted, are well known. The specific taste and aroma is to a great extent formed during roasting of the coffee beans. However, it has been found that the roasting process degrades a significant amount of the chlorogenic acids present prior to roasting. Nevertheless, the achievement of desirable "roasty" coffee flavor is of such importance to consumers, that it has hitherto been necessary to roast the beans to a significant degree with the knowledge that this will cause undesirable degradation of certain beneficial compounds. The natural chlorogenic acid content of green coffee can be reduced by as much as about 40 to 90% by weight during conventional roasting processes.

Therefore, it is highly desirable to provide a coffee product, which both retains a much higher level of chlorogenic acids than traditionally associated with roasted coffee but which nevertheless provides an acceptable and even more desirable roasted coffee flavor. Ideally, the coffee product should at least provide organoleptic properties desired by the consumer and/or avoid or minimize any undesirable organoleptic properties.

The present invention discloses a green coffee bean extract in which the concentration of chlorogenic acid (s) is significantly higher than that disclosed in commercially available samples or as disclosed in prior art processes (70-80% vs. 20-50%).

Extract of the present invention thus has considerable commercial importance in 'fortifying' either existing coffee preparations or food and drink, medicines, cosmetics, or the like, with high amounts of chlorogenic acids which are normally lost during the roasting process.

Green Coffee Beans—The term "green coffee bean" refers to either immature coffee beans or even mature coffee beans which have not been roasted. Nonvolatile and volatile compounds in green coffee beans, such as caffeine, deter many insects and animals from eating them. They also contribute to the flavor of the coffee bean when it is roasted. Nonvolatile nitrogenous compounds (including alkaloids, trigonelline, proteins and free amino acids) and carbohydrates are of major importance in producing the full aroma of roasted coffee and for its biological action. Green Coffee Beans are a rich source of chlorogenic acid and other phytochemicals which are associated with several beneficial health effects. A substantial portion of phytochemicals gets destroyed during heating and roasting of the coffee beans. Key compounds in the coffee beverage, produced from ground, roasted beans, are volatile constituents responsible for the unique aroma, the alkaloids caffeine and trigonelline, chlorogenic acids, the diterpenes cafestol and kahweal, and melanoidins, which are Millard reaction products.

Chlorogenic acid(s)—This is a trivial name used somewhat loosely in the literature to describe a range of phenolic acids found in plant materials. For example, in some literature references, 5-caffeoylquinic acid alone is referred to as "chlorogenic acid". As used herein, however, the term chlorogenic acid is used to describe one or more of a family of esters that form between certain cis or Trans cinnamic acids and quinic acid.

For the purpose of the present invention, the term 'chlorogenic acid' refers to the sum total of 7 chlorogenic acid homologues viz. 3-caffeoylquinic acid (3-CQA), 4-caffeoylquinic acid (4-CQA), 5-caffeoylquinic acid (5-CQA), 3,4 dicaffeoylqunic acid (3,4-diCQA), 3,5-dicatffeoylquinic acid (3,5-diCQA). 4,5-dicaffeoylquinic acid (4,5-diCQA), 4-feruloylquinic acid (4-FQA) and 5-feruloylquinic acid (5-FQA). The chlorogenic acid isomers may be determined by HPLC with UV detection at 320 nm using 5-CQA as external standard to calculate the concentrations. The HPLC graph obtained on analysis of green coffee bean extract of present invention, showing seven distinct peaks is as depicted in FIG. 2.

Formula: $C_{16}H_{18}O_9$; Molar mass: 354.31 g/mol and Density: 1.28 g/cm$^3$

Structure of the acid is given in FIG. 1.

Health Benefits of Chlorogenic Acid

Chlorogenic acid found in raw green coffee beans is associated with several health benefits which includes control of hypertension, blood glucose management and also weight loss. Though present in high concentrations in green coffee beans, chlorogenic acid is destroyed when the beans are 'roasted'. Raw coffee beans are the most abundant natural plant source of chlorogenic acid. Green coffee bean extract in powder form, containing about 40-50% chlorogenic acid is generally consumed as a supplement (in form of capsules) since drinking liquid coffee made from unroasted coffee beans would have a bitter unpleasant taste and would not provide the desired dosage of chlorogenic acid.

Some recent research has suggested chlorogenic acid may improve retinal health. Other research suggests that chlorogenic acid inhibits the release of glucose into the blood stream. Japanese researchers did a study in 2005 using a placebo for some participants and green coffee bean extract on the others, in a test of the potential effects of the substance on people with mild hypertension. The result was lower blood pressure and no negative side effects. Currently a lot of studies are being conducted for using green coffee bean extracts as anti-oxidant agents and treatment of life style-related diseases such as diabetes which may result due to obesity.

Dosage—The recommended dosage of Green Coffee Bean Extract as per recommendation of a commercial manufacturer (http://healthfoodpost.com/green-coffee-extract/green-cofee-bean-dosage/) is one capsule of 400 mg taken three times per day. The supplement should be taken 30 minutes before breakfast, lunch and dinner. The manufacturer warns that dosage is not to exceed (4) capsules (1600 mg) per day. Green Coffee Bean Extract contains 50% Cholorogenic Acid. Thus, the recommended safe daily dosage of Cholorogenic Acid is 600 mg (if taking 3 capsules of 400 mg each, containing 50% chlorogenic acid). The extract of present invention has higher content of Chlorogenic acids (70-80%) due to which number of capsules needed are less or for same number of capsules, better therapeutic benefits can be achieved by the consumers.

Concerns regarding presence of caffeine: Apart from Chlorogenic acids, the extract also contains trace amounts of caffeine. One capsule may contain approximately 8 mg of caffeine (3 capsules would thus contain about 24 mg of caffeine). A typical cup of regular coffee contains, on an average, 150 mg of caffeine. Some roasted coffees contain as much as 400 mg of caffeine per cup. Thus, the amount of caffeine in dietary capsules is much less than what is consumed directly as coffee drink and hence is not a cause of concern, unless a person is very sensitive to minimal amounts of caffeine.

The bioactive components in green coffee bean extract are thus 'chlorogenic acids' apart from other phytochemicals. Standardization of dietary supplements e.g. capsules is carried out in terms of content of the chlorogenic acid e.g. Green Coffee Bean extract containing 40% chlorogenic acid, 50% chlorogenic acid etc. Chlorogenic acid content of the extract thus has considerable therapeutic and commercial value.

Chlorogenic acid content of the present invention—The extract of present invention has significantly higher concentration of chlorogenic acid (almost double) than that of existing prior art or commercially available products, apart from presence of other useful phytochemicals which get destroyed during heating and roasting of the coffee beans but are present in the fraction of the invention since extraction is done without heating. The chlorogenic acid content of the fraction of present invention is about 70-80% vs. about 40-50% in commercially available fractions.

The extract of the present invention thus represents a unique product with considerably higher bioactivity in terms of anti-oxidant activity and also presence of valuable phytochemicals, which otherwise get destroyed when the green coffee beans are subjected to roasting and heating. The extract of invention is thus novel in terms of containing a significantly higher content of Chlorogenic acids (70-80%), not disclosed in prior art and elaborated for the first time in present invention along with the method for achieving the same. Further, the method of the present invention is applicable to extracts obtained from other natural source, including roasted coffee beans.

PRIOR ART PATENTS

U.S. Pat. No. 8,197,875 B2 discloses use of chlorogenic acid as an agent to offset the unpleasant or 'off-taste' of artificial sweeteners which are added to foods and drinks and the method of its extraction. The extraction method of chlorogenic acid is disclosed. It comprises use of whole green coffee beans or ground beans which are extracted with constant agitation in solvents composed of water and polar organic solvents. The organic solvents that may be used include methanol, ethanol, n-propanol, 2-propanol, acetone and propylene glycol. The beans may either be the regular beans or decaffeinated beans. They may be extracted either as whole beans or after grinding. The extraction may be carried out either with water alone or with water in combination with one or more solvents listed above. The preferred solvents are methanol and ethanol. The composition of the solvents may range between 100/0 water/organic solvent (w/w) to 10/90 water/organic solvent (w/w). The extraction temperature may be between 30° C. to 80° C. and the extraction time may be between 4 hours and 40 hours. The preferred temperature is between 45° C. to 60° C. for maximal extraction efficiency without causing significant isomerization of 5-CQA. Extraction may be carried out with equipment known to those skilled in the art, such as a counter current extractor or an extractor with constant solvent circulation.

The Chlorogenic acid content of the extract obtained by the process of this patent ranges between 35-52% only whereas it is about 70-80% in the extract of present invention.

EP1674106A1 discloses a dietetic composition comprising extract of green coffee which is prepared by extracting and separating the oil from the green coffee beans with n-hexane to yield defatted green coffee beans and preparing a polar solvent extract derived from the defatted green coffee beans with hydro ethanol having an ethanol concentration of 40 to 90% (wt./wt.).

The Chlorogenic acid content of the extract obtained by the process of this patent ranges between 20-40% only whereas it is about 70-80% in the extract of present invention.

WO 2006/108578 discloses a coffee product made from a combination of roasted and green coffee which combines the high level of antioxidants of the green coffee with the taste and aroma of roasted coffee.

The final composition contains only 8-10% chlorogenic acid which is much less than 70-80% as disclosed in present invention.

EP 2 512 260 B1 discloses a method of producing a coffee extract, comprising a) heat treating green coffee beans at a temperature between 100° C. and 180° C. for at least 5 minute, keeping the moisture level between 6% and 20% of the total weight of the coffee beans and b) extracting the treated coffee beans of step a) to produce a liquid coffee extract; wherein the coffee beans and/or the coffee extract is not subjected to roasting. The extraction of the treated green coffee beans may be performed by any suitable method, e.g. using water, ethanol, or any other suitable solvent. In a preferred embodiment, the heat treated green coffee beans are extracted with an aqueous liquid, such as water or a water based coffee extract.

The maximum concentration of chlorogenic acid in the extract as disclosed in this patent ranges from 5-11% whereas in present invention the chlorogenic acid content is 70-80%.

U.S. Pat. No. 4,938,978 describes a process whereby the moisture content of green coffee beans is increased to at least about 25% to 30% by weight based upon the weight of the moisturized beans. The moisturized beans then are heated in the presence of a substantially inert gas atmosphere under a positive pressure at a temperature sufficient and for a time sufficient for hydrolyzing and pyrolyzing the beans while substantially avoiding charring of the beans. The treated beans then are dried. The extraction yield of solids disclosed ranges from 35-41%.

Assuming 50% of the solids are chlorogenic acid, then yield of the same is only about 17.5% to about 20.5% whereas in present invention the chlorogenic acid content is 70-80%.

US 2002/0160067 A1 discloses an extraction method of preparing an extract from green coffee beans. The method involves grinding of the beans to form powder which is then extracted with an alcohol (methanol/other alcohol) water solution. The focus of the patent is to disclose that extracts rich in compounds with beneficial health effects viz. phenolic or polyphenolic compounds, which are conventionally extracted from green tea, can also be extracted from green coffee beans. The method disclosed is simple. However, the patent is silent about the concentration of chlorogenic acid in the final extract, whereas the extract of present invention contains high content (>70%) of chlorogenic acid in addition to other useful phenolic compounds.

US 2011/10189313 A1 discloses an extract prepared from green coffee beans using hydro alcoholic solvent and non-polar compound viz. hexane for defatting the beans. Defatting the beans enhances the yield of polyphenol compounds extracted, thus providing beneficial health effects and more potent extract. According to the research conducted by the inventors of this patent, the polar solvent extract of the defatted green coffee beans contains a comparatively large amount of chlorogenic acids and caffeine. Especially the dietetically-functioning chlorogenic acids are concentrated therein. More specifically, the extracts containing chlorogenic acid in concentration of 20 wt % or more and the extract containing chlorogenic acids (chlorogenic acid, ferulic acid, p-coumaric acid, coffeic acid or the like) in concentration of 45 wt % or more can greatly improve the effect of the dieting method. The concentration of chlorogenic acid in the extract of this invention is 45%. whereas extract of present invention contains high content (>70%) of chlorogenic acid in addition to other useful phenolic compounds.

From the preceding discussion, it is obvious that none of the existing processes for extraction of Green Coffee Beans result in an extract in which Chlorogenic acids content is more than 50%. The inventors in the present invention have been successfully able to prepare such an extract in which the chlorogenic acid content is very high i.e. 70-80%, thereby enhancing the nutritive as well as therapeutic value of resulting extract.

OBJECTS OF THE INVENTION

In view of the foregoing, it is an object of the present invention to provide an extract from green coffee beans, which is beneficial for health.

It is another object of the present invention to provide an extract with bio-constituents which are believed to have beneficial antioxidant properties when consumed by humans.

It is another object of the present invention to provide an extract with bio-constituents which are believed to have beneficial health properties viz. anti-tumor, anti-diabetic, anti-hypertensive and anti-obesity properties when consumed by humans.

It is another object of the present invention to provide a health-promoting extract with constituents which, while obtainable from alternative sources, are present in more beneficial quantities or ratios than are presently available through conventional source materials or through practice of conventional processes.

It is another object of the present invention to provide a new method for producing phenolic compound rich extracts.

It is another object of the present invention to provide a new method for producing phenolic compound rich extracts from green coffee beans in which concentration of the active compounds i.e. Chlorogenic acids is significantly more (70-80%) than that obtained by conventional methods (20-50%).

It is another object of the present invention to provide a new method for producing phenolic compound rich extracts with constituents which, while obtainable from alternative sources, are present in more beneficial quantities or ratios than are presently available through conventional source materials or through practice of conventional processes.

It is another object of the present invention to provide a new method for producing phenolic compound rich extracts from source materials not heretofore recognized as a practical source of such compounds.

It is another object of the present invention to provide a new method for extracting phenolic compounds from green coffee beans.

It is another object of the present invention to provide a novel extract, which may be used as a dietary supplement, flavoring, or functional food containing an extract of green coffee beans which contains polyphenolic acids and other beneficial compounds, such as diterpenes.

It is another object of the present invention to provide an improved extract processing method which yields an extract of polyphenolic acids and other beneficial compounds which are healthier than existing polyphenol extracts.

It is another object of the present invention to provide an improved extract which is more bioavailable than polyphenol extracts which are processed by conventional methods.

It is a further object of the present invention to provide an improved raw green coffee bean extract which yields a more healthful end product than existing polyphenol extracts owing to significantly higher content of chlorogenic acid (s).

A final object of the present invention is to provide an improved extract from green coffee beans which has greater ability to quench oxidative stress and destroy free radicals, than polyphenol extracts which are processed by conventional methods owing to significantly higher content of chlorogenic acid (s) of >70% than disclosed in prior art which is about 40-50%.

In satisfaction of these and related objects, the present invention is of an extract from coffee beans, which extract contains beneficial measures of phenolic acids, as well as of processes for producing such extract.

Remarkably the simple method taught herein produces an extract product which is more bioavailable, contains a healthier profile of antioxidants (phenolic compounds and chlorogenic acids) and more diterpenes (having detoxification properties) than any other existing phenolic compound-focused product (70-80% Chlorogenic acid content s 20-50% in commercially available products).

SUMMARY OF THE PRESENT INVENTION

The present invention provides an extract from green coffee beans, which is beneficial for health owing to its anti-oxidant, anti-tumor, anti-obesity, anti-hypertensive, anti-acid and anti-diabetic properties. The novel extract may be used as a dietary supplement, flavoring, or functional food containing an extract of green coffee beans. The extract contains polyphenols and bioactive compounds e.g. Chlorogenic acids in a significantly higher concentration (70-80%) than present in extracts obtained by prior art methods which contain only about 20-50% Chlorogenic acids.

This has been achieved by use of specific solvents which are less polar than alcohols and/or water immiscible such as n-Butyl alcohol, ethyl acetate or acetone, at specific stages of extraction/purification of the green coffee bean extracts. As a result the final extract is highly enriched with Chlorogenic acid fractions, as the polar impurities are left behind in the aqueous medium while the Chlorogenic acids get extracted into the low-polarity solvents. Loss of active ingredients at the intermediate stage i.e. aqueous stage is thus prevented. This results in significantly higher concentration of Chlorogenic acids in the final extract (70-80%) than that obtained in prior art methods, which used only water and alcohols (20-50%).

DETAILED DESCRIPTION OF THE INVENTION

Figure 1:
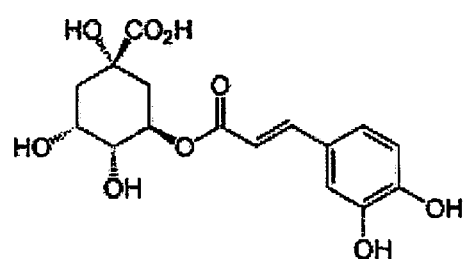
FIG. 1 shows structure of chlorogenic acid.

Chlorogenic acids are the bioactive compounds present in green coffee bean extracts and responsible for the beneficial health effects of the extracts. Such extracts are available commercially as dietary supplements in the form of capsules or tablets. Hence, a higher content of the bioactive compounds in a single dosage form is desirable so that instead of taking too many dosage forms e.g. tablets, capsules etc. a person can take a single tablet or capsule, leading to convenience for the patient and also better compliance and regularity of taking the dietary supplements.

Limitations of existing commercially available green coffee bean extracts: However, commercially available green coffee bean extracts (extracted using water and alcohol mixtures) do not have Chlorogenic acids content of more than 50%. In fact the range lies between 20-50%. There was a need and desire to have higher content of the bioactive compounds i.e. Chlorogenic acids, in the green coffee bean extracts for better therapeutic profile and also better compliance on part of person taking the extracts as dietary supplements. However, despite best efforts, enrichment of Chlorogenic acids content in the extracts beyond 50% could not be achieved, at commercial level.

Manner in which limitation was overcome in present invention: The technical problem of Chlorogenic acids content not exceeding 50% has been overcome in an innovative manner in the present invention. This has been achieved by use of specific solvents, of polarity less than that of alcohols, at specific stages of the extraction, due to which there was considerable enhancement of extraction efficiency and the Chlorogenic acids which were going waste and not getting extracted, also got extracted. This resulted in considerable enrichment of the green coffee bean extracts to 70-75% from that in prior art methods which was just 20-50%. Most of the prior art methods utilized water-alcohol mixtures for extraction and were unable to obtain an extract having Chlorogenic acids content of more than 50%, since specific solvents of lower polarity which had better affinity for Chlorogenic acids were not used at all.

Polarity of the solvents used in the present method is given below in Table 1. The table clearly shows that use of solvents of less polarity than alcohols (which have better and specific affinity for Chlorogenic acids), results in better enrichment of the green coffee bean extracts leading to much higher content of Chlorogenic acids (70-75%) in the final extracts than that obtained when using only water and alcohol mixtures.

TABLE 1

| Polarity of solvents used for extraction of Chlorogenic acids | | |
|---|---|---|
| S. No. | Solvent | Relative Polarity |
| 1. | Water | 1.000 |
| | Alcohols | |
| 2. | Ethanol | 0.654 |
| 3. | Methanol | 0.762 |
| | Solvents used for removal of fats/caffeine | |
| 4. | Hexane | 0.009 |
| 5. | Chloroform | 0.259 |
| 6. | Methylene chloride | 0.309 |
| | Solvents used for estraction of Chlorogenic acids | |

TABLE 1-continued

Polarity of solvents used for extraction of Chlorogenic acids

| S. No. | Solvent | Relative Polarity |
|---|---|---|
| 7. | Ethyl Acetate | 0.228 |
| 8. | Acetone | 0.355 |
| 9. | n-butyl alcohol (1-butanol) | 0.586 |

Data Source: Christian Reichardt, *Solvents and Solvent Effects in Organic Chemistry*, Wiley-VCH Publishers 3rd ed., 2003
(https://sites.google.com/site/miller00828/in/solvent-polarity-table)

Extraction of chlorogenic acids from other natural sources, apart from green coffee beans:

Apart from green coffee beans, the method of present invention can easily be used to prepare enriched extracts of Chlorogenic acids from other plant sources too which are rich in Chlorogenic acids viz. potatoes, bamboo (*Phyllostachys edulis*), peaches, prunes and shoots of *Calluna vulgaris* (heather). Chlorogenic acid is also found as a significant component in certain commonly used medicinal herbs (http://www.itmonline.org/arts/chlorogenic.htm). In Chinese medicine, the primary source is lonicera flowers (*jinyinhua*); Eucommia bark and gardenia fruit are also major sources, with extracts standardized to 20% chlorogenic acid. Other Chinese herbs known for their chlorogenic acid content include chrysanthemum flower, crataegus fruit, artemisia leaves, and epimedium leaves. In Western herbal medicine, an herb especially known for its chlorogenic acid content is artichoke leaves; the extracts are usually standardized to 15% of this compound. Other medicinal herbs known for content of chlorogenic acid include burdock root, dandelion root, and echinacea root. When using any of these herbs (Western or Chinese) and the concentrated herb extracts, other compounds that may contribute to a therapeutic benefit are also present. For example, artichoke leaves contain caffeol quinic acids (as found in roasted coffee) and cynarin, which is reputed to relieve abdominal gas and bloating, symptoms that occur with gallstones and poor bile flow.

Method of Present Invention for Preparing Enriched Extract of Chlorogenic Acids

The water-immiscible/solvents of less polarity than alcohols can be used either alone (thus eliminating the need for hydro-alcohol solvents altogether) or also used with hydro-alcohol solvents to enhance yields of Chlorogenic acids in extracts obtained from green coffee beans or other natural sources rich in Chlorogenic acids. Variations to the method in terms of use of different solvents (of polarity less than that of alcohols), at different stages of extraction/purification can easily be carried out by those skilled in the art and may be regarded as within the scope and disclosure of present invention.

The optimum method, in which extraction is carried out by using specific solvent ethyl acetate (having polarity of 0.228 which is lower than that of methanol having polarity of 0.762) use of alcohol is eliminated altogether is given below by way of Example 1. Embodiments in which use of specific solvents (of polarity lower than that of alcohols) along with water-alcohol mixture can result in enriched fractions of green coffee bean extract are described in Examples 2 to 4.

EXAMPLE 1

Extraction without Use of Alcohols

In this method, no alcohol is used at all in the extraction. Rather a water immiscible solvent i.e. ethyl acetate is used in the first stage itself to carry out extraction of the Chlorogenic acids. Thereafter, the extract is purified by using solvents to remove fats and caffeine. The process thus uses only three solvents in the entire process are thus water, ethyl acetate and chlorinated solvents (chloroform, methylene chloride for removal of caffeine).

Extraction: Powdered coffee beans (1 Kg or 1000 grams) are charged in a 5.0 liter flask fitted with a stirrer. 2 liter acidic water is added at 40-50° C. and gradually increased to 45-55° C. with constant stirring for 4 hours. Thereafter, 4 times the water quantity i.e. 4 liter of ethyl acetate is added and stirring is carried out at slightly elevated temperature of 50-55° C. Water and solvent mixture is filtered and the powder is transferred back to the flask. Steps of extraction with water and solvent are repeated 2-3 times, till the herb is completely exhausted. Solvent layer is separated from water and concentrated to dryness.

Purification: The dry material (dry extract) obtained is dissolved in 500 ml water. The water solution is then washed with 250 ml chlorinated solvent (Chloroform, Methylene chloride etc.) two times, to remove caffeine, which can be harmful if concentrated to excess amounts. Hence, its removal is necessary. The water is then evaporated to obtain the dry powder green coffee bean extract of present invention. No defatting step or use of solvent to remove fats is needed.

Yield and Chlorogenic acid content: 110-120 g of extract i.e. 11-12% in form of pale yellow fine powder. Content of Chlorogenic acids by HPLC is in the range of 70-80%. Analytical profile of the extract showing presence of seven distinct peaks of Chlorogenic acids, is given in FIG. 2.

EXAMPLES 2 TO 4

Extraction with Use of Alcohols

High yield can also be obtained using a combination of steps involving a hydro-alcoholic mixture and a water immiscible/miscible less polar solvent at different stages of extraction and purification respectively. Water-alcohol mixture is used for extraction. Purification is carried out by washing the extract with hexane (to remove fats) and chlorinated solvents e.g. chloroform, methylene chloride etc. (to remove caffeine). In final step of purification, water immiscible/miscible polar solvents whose polarity is less than that of methanol or ethanol i.e. n-butyl alcohol, acetone or ethyl acetate are used. This results in an extract having high Chlorogenic acid content of 70-80%.

EXAMPLE 2

Extraction Using Water-Alcohol Mixture and n-Butyl Alcohol

Extraction: Powdered coffee beans (1 Kg or 1000 grams) are charged in a 5.0 liter flask fitted with a stirrer. Water-alcohol (methanol) mixture 4 times the quantity of bean powder i.e. 4 liters, is added at 40-50° C. and gradually increased to 45-55° C. with constant stirring for 4 hours. Water and alcohol mixture is filtered and the powder is transferred back to the flask. Steps of extraction with water and alcohol are repeated 2-3 times, till the herb is completely exhausted. The polar compounds thus get extracted into the hydro-alcoholic mixture. The mixture is then concentrated by vacuum and volume reduced to 800-1000 ml inside the vessel.

Purification: Defatting of the aqueous layer is carried out by washing the aqueous layer obtained with 500 ml each of hexane, twice. After removal of fats, aqueous layer is washed with chlorinated solvent e.g. Chloroform, Methylene chloride etc. thrice with 600 ml each, to remove caffeine. The aqueous layer now free from fats and caffeine, is rich in chlorogenic acids. It is acidified and extracted with n-Butyl alcohol thrice with 600 ml each, to extract the chlorogenic acids. The extracts are combined and concentrated to dryness to obtain the final green coffee bean extract having high content of Chlorogenic acids.

Yield and Chlorogenic acid content: The yield obtained is 90-100 g i.e. 9-10% in form of pale yellow fine powder. Content of Chlorogenic acids by HPLC is in the range of 70-80%. Analytical profile is similar to that given in FIG. 2.

EXAMPLE 3

Extraction Using Water-Alcohol Mixture and Acetone

Extraction: Carried out using the water-alcohol mixture, as described in Example 2.

Purification: Instead of n-butyl alcohol, another polar solvent having polarity less than that of alcohol i.e. acetone is used. Other steps remain the same.

Yield and Chlorogenic Acid Content: Yield obtained is 100-110 g i.e. 10-11% in form of pale yellow fine powder. Content of Chlorogenic acids by HPLC is in the range of 70-80%. Analytical profile is similar to that given in FIG. 2.

EXAMPLE 4

Extraction Using Water-Alcohol Mixture and Ethyl Acetate

Extraction: Carried out using the water-alcohol mixture, as described in Example 2.

Purification: Instead of n-butyl alcohol, another polar solvent having polarity less than that of alcohol i.e. ethyl acetate is used. Other steps remain the same.

Yield and Chlorogenic Acid Content: Yield obtained is 75-90 grams i.e. 7.5-9% in form of pale yellow fine powder. Content of Chlorogenic acids by HPLC is in the range of 70-80%. Analytical profile is similar to that given in FIG. 2.

HPLC Analytical Conditions

The HPLC analytical conditions followed for analysis of the extract. as described in the examples above obtained are elaborated below.

Reference solution preparation: 30 mg green coffee bean extract working standard is taken in 50 ml volumetric flask. 40 ml diluent is added and sonication carried out for 10 min. Final volume is made up with diluents. Solution is shaken well and filtered with 0.45µ filter.

Test solution preparation: 30 mg green coffee bean extract sample is taken in 50 ml volumetric flask. 40 ml diluents are added and sonication is carried out for 10 min. Final volume is made up with diluents. Solution is shaken well and filtered with 0.45µ filter.

Chromatographic assessment of purity: The solvent flow rate, analytical column type, flow rate conditions etc. are as described below:

| S. No. | Description | Chromatographic conditions |
|---|---|---|
| 1. | Celumn | Luna 5µ C 18(2) 250 × 4.6 mm |
| 2. | Flow Rate | 1.5 ml/min |
| 3. | Detector | UV, 330 nm |
| 4. | Run Time | 40.0 min |
| 5. | Column Oven Temperature | 25° C. |
| 6. | Diluents phase | Acetonitrile:Formic Acid:Water (10:2:90) |

Calculation:

$$\text{Chlorogenic acid Content } (\% \ w/w) = \frac{\text{Test area}}{\text{Standard area}} \times \frac{\text{Concentration of standard}}{\text{Concentration of test}} \times \% \text{ potency/purity of standard}$$

Figure 2:
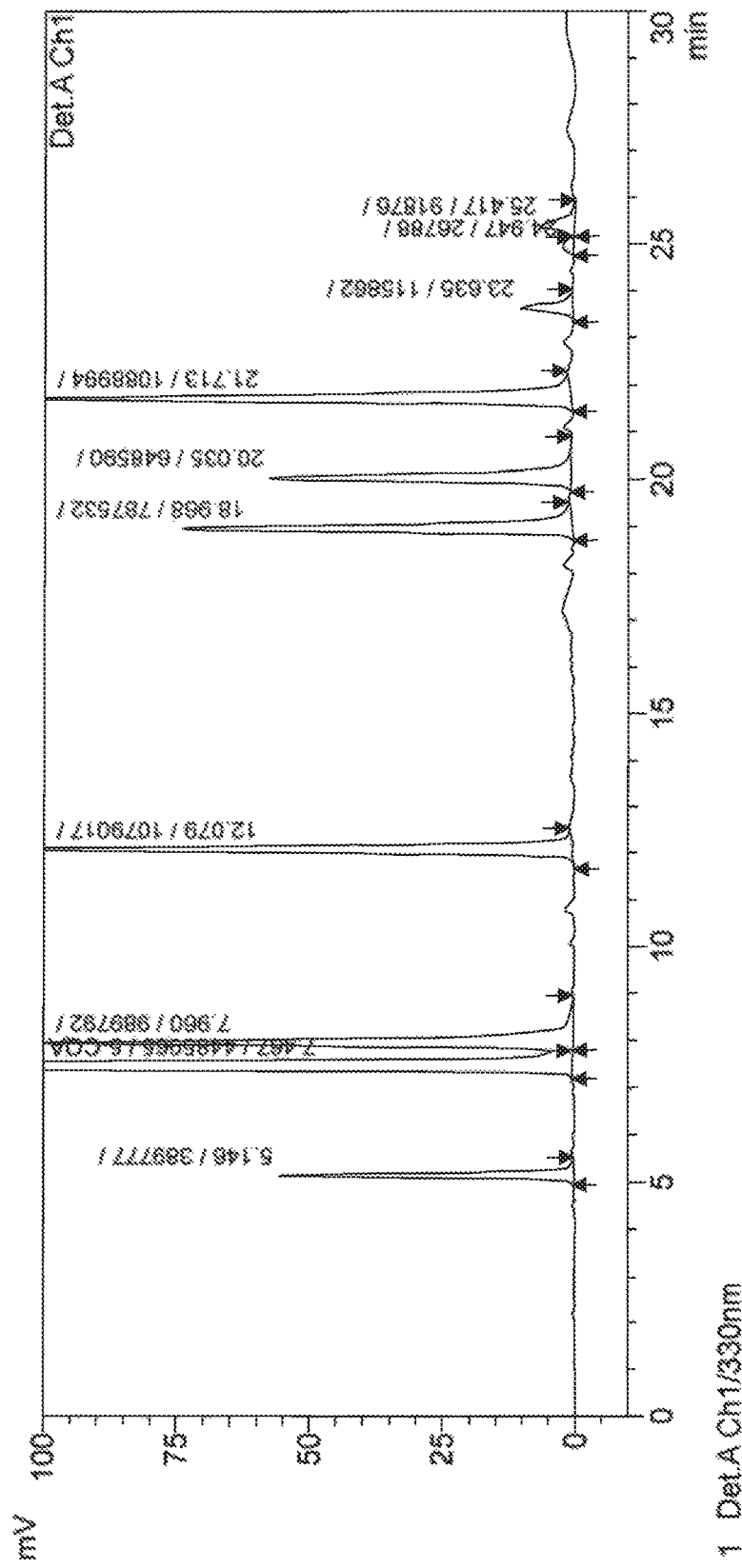
FIG. 2 shows analytical and physical data of chlorogenic acids.
Figure 3:
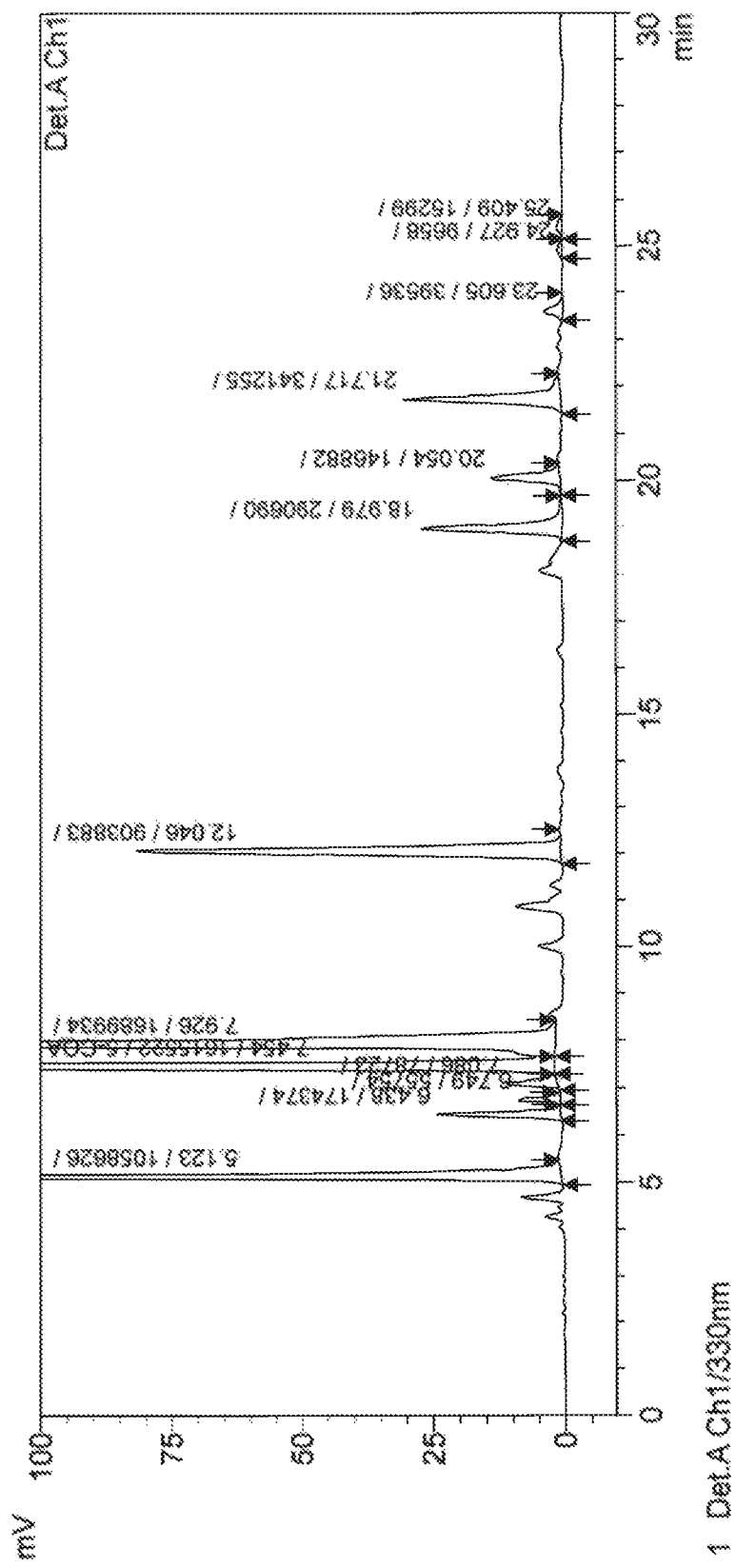
FIG. 3 show analytical and physical data of commercially available sample of green coffee bean extract.

From the above table and examples it is clear that the modified process of the present invention results in a green coffee bean extract in which the content of the bioactive compounds i.e. total chlorogenic acids is much higher viz. 70-80% than extracts mentioned in any of the prior art patents and the extract has a unique and distinctive composition owing to use of specific and distinctive polar solvents having polarity lower than that of alcohols used in the extraction process viz. methanol or ethanol. In the present invention, use of solvents having less polarity than alcohols, resulted in extraction of enriched Chlorogenic acid fractions, leaving the polar impurities in the aqueous medium. The extract of the present invention accordingly has a considerably improved therapeutic profile owing to higher concentration of the bioactive compounds (Chlorogenic acids and other polyphenol compounds) present in the extract of present invention and also higher purity, as evident from clear peaks of Chlorogenic acids (FIG. 2). In contrast, a commercially available sample of green coffee bean extract when analyzed not only shows much lower content of chlorogenic acids, but also several other additional peaks (FIG. 3), thus indicating presence of other compounds which are absent in the extract of present invention.

We claim:

1. A method to produce an enriched extract having chlorogenic acids content ranging between 70-80 weight %, from dried coffee beans, wherein the method comprises the steps of:
    i. powdering the dried coffee beans;
    ii. extracting the powdered coffee beans by adding a water-alcohol mixture in quantity four times the dried coffee beans by volume and stirring at a temperature between 45-55° Celsius for 4 hours to form a mixture;
    iii. filtering the mixture;
    iv. repeating the extraction of steps ii) and iii) 2-3 times until the powdered coffee beans are completely exhausted and a hydro-alcoholic mixture is obtained;
    v. concentrating the hydro-alcoholic mixture by vacuum to reduce the volume to one fourth and to obtain an aqueous layer;
    vi. removing fats from the aqueous layer by washing with hexane;
    vii. removing caffeine by washing with a chlorinated solvent;
    viii. extracting chlorogenic acids with a polar solvent which has polarity less than that of alcohols; and
    ix. evaporating the polar solvent to obtain a dry powder extract in which the content of chlorogenic acids ranges between 70-80 weight % wherein the step of removing caffeine by washing with a chlorinated solvent takes place after the powdered coffee beans are extracted by adding the water-alcohol mixture.

2. The method according to claim 1, wherein the polar solvent is n-butyl alcohol.

3. The method according to claim 1, wherein the polar solvent is acetone.

4. The method according to claim 1, wherein the polar solvent is ethyl acetate.

5. The method according to claim 1 wherein the chlorinated solvent is selected from chloroform and methylene chloride.

* * * * *